US00RE34110E

United States Patent [19]

Opie, deceased, et al.

[11] E Patent Number: Re. 34,110

[45] Reissued Date of Patent: Oct. 27, 1992

[54] ENDOSCOPE FOR USE WITH A DISPOSABLE SHEATH

[75] Inventors: Eric A. Opie, deceased late of Brier, Wash. by Elizabeth J. Terry, Brier, Wash., executrix, Fred E. Silverstein, Seattle, Wash.

[73] Assignee: Opielab, Inc., Seattle, Wash.

[21] Appl. No.: 727,224

[22] Filed: Jun. 25, 1991

Related U.S. Patent Documents

Reissue of:

[64] Patent No.: 4,869,238
Issued: Sep. 26, 1989
Appl. No.: 185,116
Filed: Apr. 22, 1988

[51] Int. Cl.[5] ..... A61B 1/00
[52] U.S. Cl. ..... 128/6
[58] Field of Search ..... 128/4, 5, 6, 7

[56] References Cited

U.S. PATENT DOCUMENTS

| | | | |
|---|---|---|---|
| 2,797,683 | 7/1957 | Aiken | 128/6 |
| 3,739,770 | 6/1973 | Mori | 128/6 |
| 4,024,858 | 5/1977 | Chikama | 128/4 |
| 4,606,330 | 8/1986 | Bonnet | 128/7 |
| 4,646,722 | 3/1987 | Silverstein et al. | 128/4 |
| 4,721,097 | 1/1988 | D'Amelio | 128/4 |

FOREIGN PATENT DOCUMENTS

| | | |
|---|---|---|
| 184778 | 5/1985 | European Pat. Off. . |
| 2150595 | 10/1971 | Fed. Rep. of Germany . |

*Primary Examiner*—William H. Grieb
*Attorney, Agent, or Firm*—Seed and Berry

[57] ABSTRACT

An endoscope specially adapted for use with a disposable sheath having an outer casing and one or more internal channels. The endoscope includes a tip portion connected to a control handle through a flexible insertion tube. The insertion tube is formed by a braided wire tube covered by a flexible waterproof coating and surrounding a resilient D-shaped tube through which optical components for the endoscope extend. A longitudinally extending groove is formed in the braided tube to receive and channel(s). The groove extends perpendicular to, and makes contact with, a generally planar portion of the D-shaped tube so that the D-shaped tube can restrict deformation of the groove as the insertion tube bends. Longitudinal channels are formed on opposite sides of the groove to house control cables extending from the control handle to the tip portion. The cables are surrounded by tubes that collectively occupy the entire channel so that the tubes prevent the channel, and hence the groove, from collapsing.

29 Claims, 2 Drawing Sheets

FIG. 1
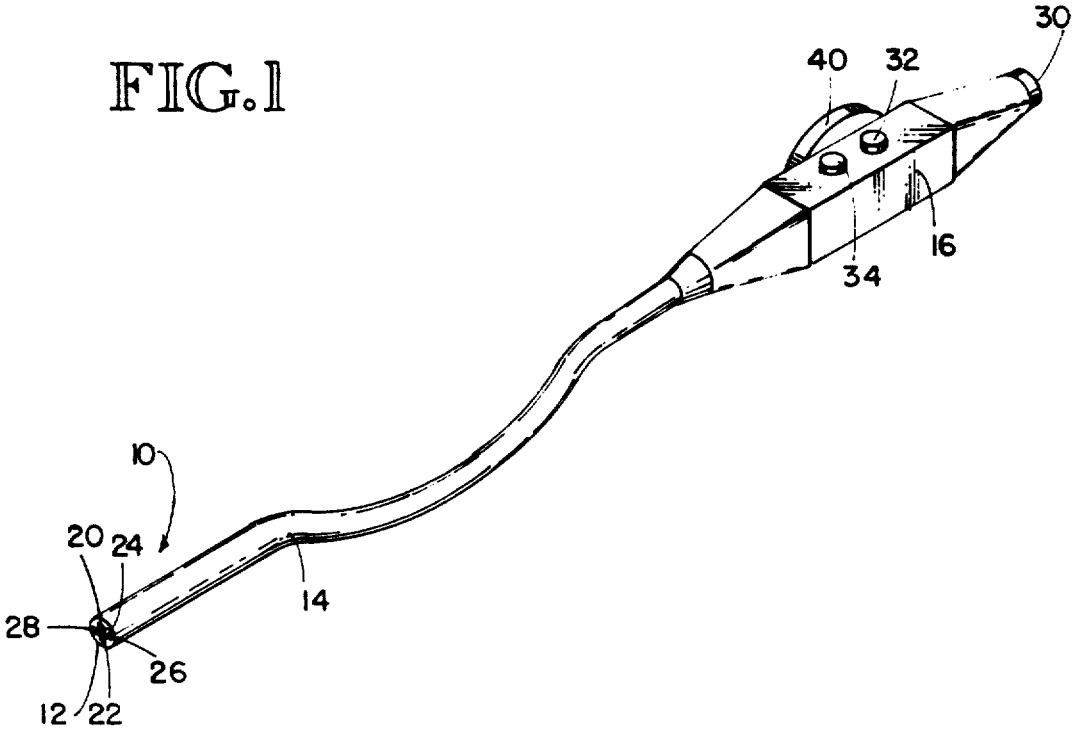
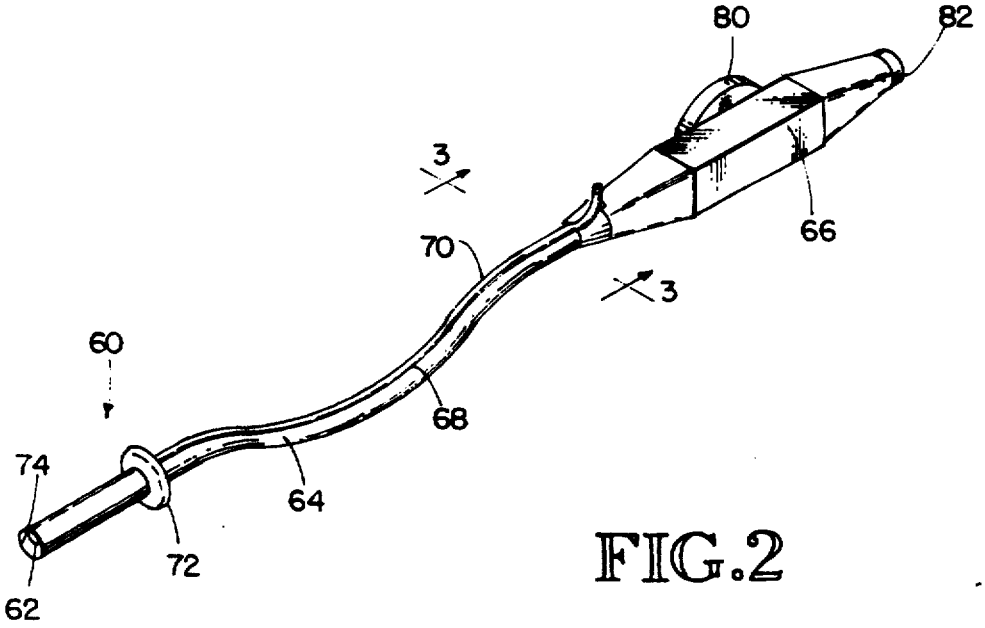
FIG. 2

ENDOSCOPE FOR USE WITH A DISPOSABLE SHEATH

Matter enclosed in heavy brackets [ ] appears in the original patent but forms no part of this reissue specification; matter printed in italics indicates the additions made by reissue.

TECHNICAL FIELD

This invention relates to the field of endoscopy, and more particularly, to the construction of the basic endoscope core of a device for inexpensively isolating an endoscope from virus and bacteria.

BACKGROUND ART

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as "flexible sigmoidoscopes," are good examples of the usefulness of endoscopic technology. These devices are expensive, and they are used in a contaminated environment for a procedure which is brief (five to ten minutes) and where problems of cleaning time and contamination are important factors. There has been a large increase in the use of the flexible sigmoidoscope for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning, requiring on the order of eight to ten minutes, may not allow adequate cleaning, particularly in view of the increasing problems with contagious viruses. Even with the use of chemicals such as gluteraldehyde, adequate cleanliness may not be possible.

The cleaning problem not only includes the outside of the endoscope, but also the multiple small channels inside the endoscope. This includes channels for: air insufflation; water to wash the tip; and biopsy and suction. Each channel also has a control valve. These channels extend along the length of the endoscope and come into contact with body tissues and fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing some types of endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each of the many types described above makes this solution impractical especially for physicians offices and smaller clinics.

Not only must the idle time of the physician be added to the cost of endoscopic examinations, but the same spent by a nurse or other hospital personnel in the cleaning as well as the cost of disinfecting chemicals and other costs of the cleaning process must also be added to the cost of the examination. Although automatic washing machines are available to clean endoscopes, these machines are expensive, take up significant amounts of space, are noisy, and are not faster than washing by hand. Further, regardless of whether the cleaning is done manually or by machine, the cleaning chemicals can be harmful to the endoscope and thus significantly shorten its life. The cleaning chemicals, being toxic, are also potentially injurious to the staff who use them and to the environment into which they are discharged. To use some of these chemicals safely, such as gluteraldehyde, requires a dedicated ventilated hood, which uses up space and is expensive to install and operate. The chemicals are also potentially toxic to the patient in that, if residue remains after cleaning and rinsing the instrument, the patient could have a reaction to the chemicals.

As a result of these many problems, conventional endoscope cleaning techniques greatly increase the cost of endoscopic procedures. Furthermore, while the risk of contamination using endoscopes is often far less than the risk of alternative procedures, such as surgery, there is nevertheless a risk that endoscopes are not cleaned adequately to prevent the risk of transmission of infectious diseases from one patient to the next.

In the health care field, the problem of contaminated instruments transmitting disease from one patient to the next have generally been solved by making such instruments disposable. However, this approach has not been thought possible in the field of endoscopy because endoscopes are very expensive instruments. Moreover, it has not been thought possible to isolate the endoscope from the patient or the external environment because the endoscope itself has channels inside it that are used as conduits for body fluids and tissues, such as, for example, in taking biopsies. The only method currently available to actually sterilize an endoscope is to use gas sterilization with ethylene oxide gas. However, there are several disadvantages in using this procedure. The procedure is very slow (up to 24 hours), during which time the endoscope cannot be used. Also, the gas affects the plastic of the endoscope and may limit its lifespan. Finally, the gas is toxic and, therefore, great care must be taken to ensure that no residue remains that might cause patient or staff irritation or allergic reaction during contact with the endoscope.

As a result of the above-described limitations in using and cleaning endoscopes by conventional techniques, there has not heretofore been an acceptable solution to the problem of making endoscopy procedures both inexpensive and entirely safe.

A new approach to the problem of endoscope contamination is described in U.S. Pat. No. 4,646,722. This new approach involves the use of an endoscope sheath having a flexible tube surrounding the elongated core of an endoscope. The flexible tube has a transparent window near its distal end positioned in front of the viewing window of the endoscope. Channels that come into contact with the patient or the patient's body fluids (e.g., channels for taking biopsies, injecting air or injecting water to wash the window of the sheath) extend along the endoscope, either inside or outside the sheath. Where the channels are positioned inside the sheath, they may be inserted in a longitudinal groove formed in the endoscope core. The protective sheath may be used with either end-viewing endoscopes or side-viewing endoscopes. The protective sheath may be installed by rolling the elastomeric tube into an annular configuration and then unrolling the tube over the core of the endoscope. Alternatively, the tube may be inflated in its unrolled configuration to expand the tube and allow it to be easily slipped onto the endoscope core. A variety of specialized endoscopes may be created by using protective sheaths having a variety of special purpose medical instruments mounted at the end of a biopsy channel and operated through the channel.

The endoscope used in the implementation of the above-described concept in one configuration must have a groove formed along its length. A tube is inserted into this groove to provide channels for air, water and suction. Once the groove is inserted, it is covered with the sheath. After use, the sheath and channel insert are removed and disposed of, leaving the endoscope free of contamination resulting from the endoscopic procedure. Construction of a flexible, strong, torque-stable endoscope with a groove requires new approaches to endoscope construction. Standard flexible endoscopes are constructed of an armor, usually consisting of three layers: one or more metal coils, usually manufactured from wire ribbon in a helical pattern to give the device compressive strength; a wire mesh to give the outer surface continuity to partially control flexibility and torque stability; and a plastic polymer to make the tube fluid-tight and to entrap the wire mesh braid to control flexibility and to add some torque stability. The plastic also provides a slippery surface to facilitate passage of the endoscope.

The conventional endoscope structure described above is unstable for shapes other than round, for example, with a groove along its length. If the armor coil is simply indented, it loses flexibility and compressive strength, both of which are essential for endoscopes. Because of its heavy use in a variety of environments by a variety of personnel, endoscopes must have acceptable strength to avoid collapse of the walls, resulting in injury to the delicate and expensive optical system (fiberoptic or video) and light system. It is also essential to ensure that the endoscope wall is thin to keep the overall diameter of the endoscope as small as possible to improve patient compliance and to make as much room available as possible for elements inside the tube. For example, the biopsy channel should be as large as possible to provide the best instrument function. Finally, manipulation of the controls of the endoscope must be directionally insensitive so that the endoscope will react in the same manner regardless of the direction in which it is manipulated. Ideally, the endoscope should have the same "feel" as conventional endoscopes.

DISCLOSURE OF THE INVENTION

It is the object of the invention to provide an endoscope that is flexible, strong and torque stable and has a groove along its length so that it can be used with a disposable sheath, as described in U.S. Pat. No. 4,646,722.

It is another object of the invention to provide an endoscope having a longitudinal groove for receiving the channel(s) of a disposable sheath that operates in the same manner as conventional endoscopes and that has the same "feel" as conventional endoscopes.

It is another object of the invention to provide an endoscope having a longitudinal groove for receiving the channel(s) of a disposable sheath that has uniform control characteristics in all directions.

It a still another object of the invention to provide an endoscope having a longitudinal groove for receiving the channel(s) of a disposable sheath that is substantially as sturdy as conventional endoscopes so that it can withstand heavy clinical use.

It a further object of the invention to provide an endoscope having a longitudinal groove for receiving the channel(s) of a disposable sheath that is constricted in a manner that prevents the groove from collapsing when the endoscope is bent.

These and other objects of the invention are provided by an endoscope having a tip portion including an optics window, a control handle having a set of controls for controlling the angular orientation of the tip portion, an insertion tube extending between the tip portion and the control handle, and an imaging system. The core of the insertion tube is a resilient, D-shaped tube through which the components of the imaging system extend. The D-shaped tube is positioned within a braided tube, with the braided tube abutting a cylindrical portion of said D-shaped tube. A longitudinal groove is formed in the braided tube diametrically opposite the D-shaped tube, and a coating of a flexible, waterproof material is bonded to the outer surface of the braided tube. The portion of the braided tube forming the groove preferably contacts the D-shaped tube so that the D-shaped tube can stabilize the groove. A plurality of longitudinally spaced wires may extend from one side of the insertion tube to the other adjacent the apexes of the D-shaped tube to prevent the insertion tube from deforming in a direction transverse to the plane of the groove. A pair of channels may be formed in the insertion tube on opposite sides of the groove to house a plurality of control cables extending from the control handle to the tip portion. The control cables are surrounded by respective flexible tubes that may collectively occupy substantially all of the volume contained within the channels. As a result, the tubes surrounding the control cables can prevent the walls of the groove from collapsing. The insertion tube may also include a plurality of longitudinally spaced ribs extending between the apexes of the D-shaped tube. Each of the ribs has a pair of semicylindrical walls separated by an inwardly extending, U-shaped section conforming to the shape of the groove. The ribs stabilize the insertion tube and groove as the insertion tube bends.

BRIEF DESCRIPTION OF THE DRAWINGS

FIG. 1 is an isometric view of a conventional endoscope.

FIG. 2 is an isometric view of the inventive endoscope ready for use with a disposable sheath, having a biopsy channel positioned in a longitudinal groove formed in the endoscope.

BEST MODE FOR CARRYING OUT THE INVENTION

Figure 3:
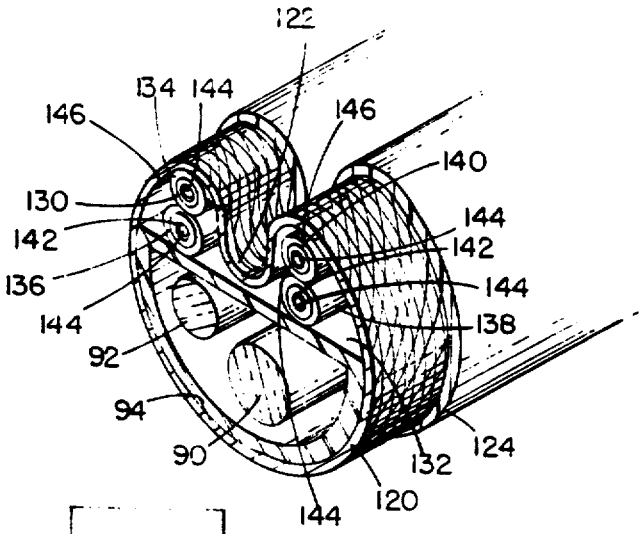
FIG. 3 is an isometric sectional view taken along the line 3—3 in FIG. 2, with the disposable sheath removed for clarity of illustration.

The inventive endoscope, like the conventional endoscope 10 illustrated in FIG. 1, includes a tip portion 12, a flexible insertion tube 14, and a control handle 16.

The tip portion 12 includes an optics window 20, a biopsy port 22, a water nozzle 24 for cleaning the optics window 20, a suction port 26 for suctioning body fluids, and an inflation port 28 for inflating body cavities so that the walls of the cavities may be more easily examined. The optics window 20 encloses an imaging system (not shown) and an illumination system (not shown). The imaging system may be either video or fiberoptic, i.e., either a miniature television camera of a set of aligned optical fibers. The illumination system may be either electrical or fiberoptic, i.e., an electrically powered light or an optical fiber that receives light externally.

The insertion tube 14 is an elongated, flexible noncollapsible tube that contains a biopsy channel (not shown) communicating with the biopsy port 22, a water channel (not shown) communicating with the water nozzle 24, a suction channel (not shown) communicating with the suction port 26, and an inflation channel (not shown) communicating with the inflation port 28. The insertion tube 14 also contains wires for communicating with a television camera and light if a video imaging system is used or, alternatively, optical fibers terminating at the optics window 20 if a fiberoptic imaging system is used. Finally, the insertion tube 14 contains control cables (not shown) extending between the control handle 16 and the tip portion 12. As explained below, the control cables bend the tip portion 12 as desired to point the optics window 20 in the desired direction.

The control handle 16 performs several functions. In the event that a fiberoptic imaging system is used, the optical fiber terminates at an eyepiece 30 through which the clinician can view an image of the tissue in front of the optics window 20. The control handle 16 also includes a connector (not shown) for connecting a light source to the illuminating optical fiber extending to the optical window 20. If a video imaging system is used, the control handle 16 normally includes an electrical connector (not shown) for applying the television signal to a monitor and for powering the light behind the optics window 20. The control handle 16 also includes a manually actuatable valve 32 for the suction channel and a single manually actuatable valve 34 for both the inflation channel and the water channel. The control handle 16 also includes ports for these channels and for the biopsy channel. The control handle 16 also includes several controls, designated collectively as 40, that control the bending of the tip portion 12, as mentioned above. Each of the controls 40 retracts one control cable while extending an opposite control cable. As mentioned above, the control cables extend through the insertion tube 14 and terminate in the tip portion 12. The control cables 40 are arranged so that retracting one cable while allowing another cable to extend bends the tip portion 12 in the direction of the retracted cable. Conventional endoscopes generally include two controls 40 in the form of concentric wheels. One control 40 bends the tip portion 12 up and down while the other control 40 bends the tip portion 12 right and left.

It is important to note that the conventional endoscope 10 illustrated in FIG. 1 is radially symmetric. This radial symmetry allows the endoscope 10 to have uniform control characteristics regardless of the direction in which the tip portion 12 is directed. In other words, the torque and rotation angle required to rotate the up-down control to bend the tip portion 12 up by a predetermined amount can be the same as the torque and rotation angle required to rotate the right-left control to bend the tip portion 12 to the right by that same amount.

In operation, the clinician advances the tip portion 12 into a body cavity, such as the stomach or colon. The cavity is then inflated, if it is desired to make the walls of the body cavity more visible, by actuating the valve 34 communicating with the inflation channel. The clinician can then examine the walls of the cavity by manipulating the controls 40 to point the optics window 20 in any desired direction. If the window 20 becomes covered with blood, etc., during the examination, the valve 34 communicating with the water channel is actuated to spray water from the nozzle 24. Also, if the clinician desires to withdraw fluid from the body cavity, the valve 32 communicating with the suction channel is actuated. If the clinician wants to biopsy the wall of the body cavity or perform a surgical procedure, an appropriate instrument is inserted through the biopsy channel and out through the biopsy port 22 so that it can be viewed through the optics window 20 while performing the biopsy or other procedure.

It is readily apparent that the endoscope 10 will become contaminated during the above-described procedure. Further, the contamination will occur not only on the outside of the endoscope, but it will occur also in the biopsy, suction and possibly other channels that are internal to the endoscope. Those internal channels are extremely difficult, if not impossible to adequately clean, even if a great deal of time and effort are devoted to the cleaning procedure. Further, the chemicals used to perform the cleaning can damage the endoscope, they are fairly expensive, and they can be toxic to the patient if significant residue remains after the cleaning.

In order to avoid these contamination and cleaning problems, a disposable endoscope sheath was developed, as described in U.S. Pat. No. 4,646,722. Although conventional endoscopes could be easily adapted for use with the disposable endoscope sheath, the resulting endoscope would be less than ideal for a number of reasons. The endoscope would not have the "feel" and uniform control characteristics of conventional endoscopes, primarily because the groove formed in the endoscope for receiving the biopsy channel of the sheath would the destroy the radial symmetry. Also, merely placing a groove in a conventional endoscope, might cause the groove to collapse to some extent under certain bending configurations.

One embodiment of an endoscope that has been specially adapted for use with a disposable endoscope sheath is illustrated in FIG. 2. The endoscope 60, like conventional endoscopes, includes a tip portion 62, an insertion tube 64, and a control handle 66. An elongated, generally U-shaped groove 68 extends along the length of the insertion tube 64 and the tip portion 62. The groove 68 receives the biopsy channel 70 (and, if desired, water, suction and inflation channels) formed in a disposable sheath 72 that surrounds the endoscope 60. The end of the sheath 72 includes an optical window 74 for an imaging system and an illuminating system in the tip portion 62 of the endoscope 60. As with conventional endoscopes, the imaging system may be either video or fiberoptic. Similarly, the illuminating system may be either electrical or fiberoptic. The endoscope 60 also includes a set of control cables (not shown) extending through the insertion tube 64 from the tip portion 62 to the control handle 66 for selectively bending the tip portion 62 as desired. The control cables are operated by conventional controls 80 mounted on the control handle 66. The control handle 66 also includes a conventional eyepiece 82, assuming that a fiberoptic imaging system is used. The control handle 66 is very similar to the control handles of conventional endoscopes. The major difference is that the normal valve arrangement of conventional endoscopes cannot be used since the channels communicating with those valves do not extend through the endoscope 60. Instead, in the event that the sheath includes channels in addition to the biopsy channel 70, the channels will extend to an external valve mechanism of conventional design.

The endoscope 60, illustrated in FIG. 2, can most advantageously be used with a disposable endoscope sheath if it satisfies a number of optimum design goals. These goals are: relatively small diameter (less than 2.0 cm in diameter); flexibility (radius of curvature of 3 cm); space inside for up to four control cables to control the bending of the tip section 12; protected space for the imaging system (fiberoptic or video); protected space for illuminating system; torque stability; strength to resist compression and distortion; and a groove 68 along its length large enough to receive multiple channels (usually air, water, suction and biopsy) yet constructed so that it will not collapse when the endoscope bends.

Figure 4:
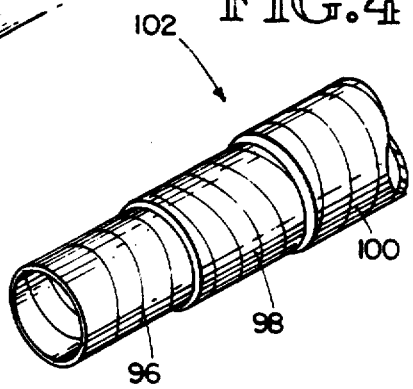
FIG. 4 is a broken isometric view of a specially configured cylindrical coil used to form a principal component of the inventive endoscope.

The construction of the inventive endoscope 60 is shown in greater detail in FIG. 3. The optical components of the endoscope, shown here as a set of aligned optical fibers 90 and an illuminating optical fiber 92, extend through a D-shaped flexible tube 94. The components 90, 92 may also be an electrical cable extending to a miniature television camera behind the optics window 74 and a pair of electrical conductors extending to a light mounted behind the optics window 74. The D-shaped tube 94 is preferably formed of at least three concentric helical coils 96, 98, 100 of thin, springsteel ribbons, as illustrated in FIG. 4. Adjacent coils are wound in opposite directions so that the inner coil is wound in a helical direction, the middle coil is wound is an antihelical direction, and the outer coil is wound in a helical direction. Winding the coil in this manner gives it excellent torque stability and allows the layers to slide over each other without the edges of adjacent layers catching each other when the tube 94 is bent. The resulting cylindrical tube 102 is very strong and flexible.

Figure 5:
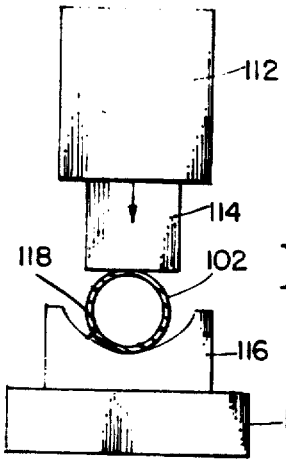
FIG. 5 is a cross-sectional view showing a method of forming a D-shaped tube from the cylindrical tube illustrated in FIG. 4.

The D-shaped tube 94 is formed from the cylindrical tube 102 using a conventional press, as illustrated in FIG. 5. As is well known in the art, the press includes a lower, stationary press member 110 and an upper press member 112 that moves downwardly toward the lower member 110 with a great deal of force. An elongated flat bar 114 is mounted on the lower end of the upper press member 112, and an elongated die 116 containing a semicircular cutout 118 is placed on the lower press member 110. The circular tube 102 is placed in the circular cutout, and the upper press member 112 is lowered until the bar 114 has flattened the cylindrical tube 102 so that it then becomes a D-shaped tube 94. In this configuration, the tube 94 maintains all of the essential characteristics including flexibility, torque stability, and strength, found in the cylindrical tube 102.

Returning now to FIG. 3, the D-shaped tube 94 is placed inside the lower portion of a tube 120 of wire braid or mesh. An elongated groove 122 is then formed in the upper portion of the braided tube 120, and the tube 120 is coated with a suitable polymer coating 124. The polymer coating 124 seals the braided tube against moisture, and it controls the flexibility of the endoscope. More specifically, the flexibility of the endoscope is controlled by the durometer and thickness of the polymer coating 124.

It is important to note that the bottom of the groove 122 contacts the upper surface of the D-shaped tube 94. This configuration allows the noncompressive characteristic of the D-shaped tube to prevent the groove 122 from narrowing and elongating (i.e., becoming deeper) when the endoscope is bent in a direction transverse to the plane of the groove (i.e., to the right or left, as shown in FIG. 3). The D-shaped tube 94 thus functions to stabilize the shape of the groove 122.

The D-shaped tube 94 and the groove 122 form two channels 130, 132 inside the braided tube 120 on either side of the groove 122. Each of these channels 130, 132 houses a pair of flexible tubes 134, 136 and 138, 140, respectively. These tubes 134–140, like the cylindrical tube 102 described above with reference to FIG. 4, are formed from one or more coils of helically wound wire ribbon. However, they are small in diameter in order to fit into the channels 130, 132, and they are either left round or slightly deformed to conform to the shape of the channels 130, 132. The tubes 134–140 house cable covers 142 and control cables 144 that are used to control the bending of the tip portion 62, as described above. In addition to housing the control cable 144, the tubes 134–140 also strengthen the endoscope and help retain the shape of the groove 122 since it is not possible to compress the sides of the groove 122 in a vertical manner with the tubes 134–140 in place. To further stabilize the shape of the endoscope, all or part of the channels 130, 132 around the tubes 134–140 can be filled with a flexible polymer 146, such as silicone. Filling the channels 130, 132 in this manner can improve localization of the inner components and improve the compressive strength of the overall assembly.

As explained above, the tubes 134–140 stabilize the shape of the endoscope and groove 122 for bending of the endoscope in the plane of the groove 122 (i.e., up and down in FIG. 3), while the D-shaped tube 94 stabilizes the shape of the endoscope and the groove 122 for bending transverse to the plane of the groove. However, additional stabilization may be desirable in order to keep the braided tube 120 from pulling away from the apexes of the D-shaped tube 94 responsive to transverse bending. The endoscope is preferably stabilized for transverse bending by weaving a fine wire 150 back and forth along the length of the endoscope. The wire 150 holds in the sides of the braided tube just above the diameter of the D-shaped tube 94. The wire 150 could also extend back and forth between the tubes 134, 138 in the channels 130, 132. Alternatively, stabilization against transverse bending could be provided by using a suitable adhesive to bond the braided tube 120 to the D-shaped tube 94.

Figure 6:
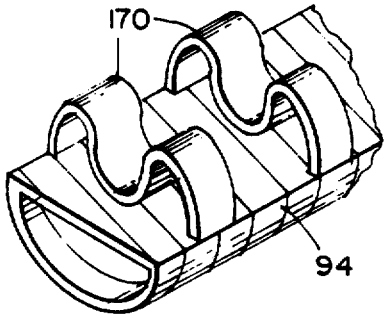
FIG. 6 is an isometric view of an alternative construction of the inventive endoscope.

An alternative embodiment, illustrated in FIG. 6, is similar to the embodiment of FIG. 3 in that it also uses a D-shaped tube 94 surrounded by a braided tube 120 (FIG. 3) in which a groove 122 is formed and the tube 120 is covered with a polymer coating 124. However, the embodiment of FIG. 6 utilizes a plurality of longitudinally spaced ribs 170 attached, such as by welding, to the apexes of the D-shaped coil 94. The ribs 170 have the desired shape of the upper portion of the endoscope, including the groove 122, and they provide rigid side walls for the groove 122. The ribs are preferably fabricated from steel so that they are sufficiently strong to prevent vertical compression of the grooves 122 as well as lateral expansion of the endoscope with bending. Flexibility is controlled by the spacing between the support ribs 170. The support ribs 170 do not contribute to flexibility or torque stability of the endoscope, but they add significantly to the overall strength and non-collapsibility of the endoscope.

Figure 7:
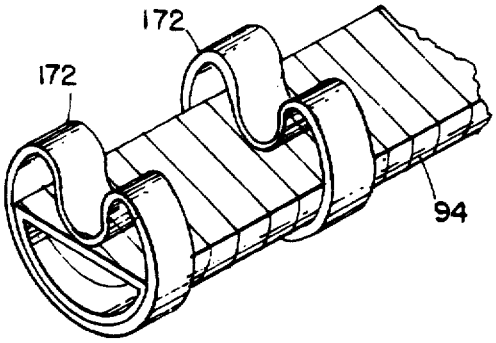
FIG. 7 is an isometric view of another alternative construction of the inventive endoscope.

With reference to FIG. 7, a slight variation of the embodiment illustrated in FIG. 6 utilizes ribs 172 that have lower portions that are cylindrical in shape such that they wrap around the D-shaped tube 94. The ribs 172 may float on the D-shaped tube 94, or they may be bonded to either the D-shaped tube 94 or to the braided tube 120.

Figure 8:
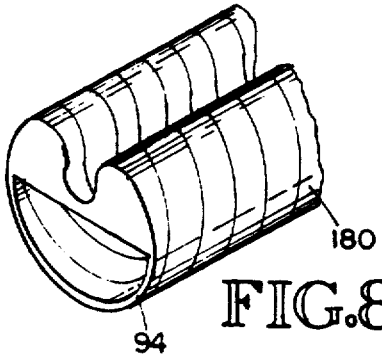
FIG. 8 is an isometric view of still another alternative construction of the inventive endoscope.

With reference to FIG. 8, still another embodiment of the invention utilizes a formed helical coil 180 that is wrapped around the D-shaped tube 94. The coil 180 can be attached to the tube 94 or it can free float on the tube 94.

The inventive endoscope thus has a groove along its length so that it can be used with a disposable sheath as described in U.S. Pat. No. 4,646,722, yet it is flexible, strong and torque stable. Furthermore, it operates in the same manner and with the same "feel" as conventional endoscopes, and it has uniform control characteristics in all directions.

We claim:

1. An endoscope for use with a disposable sheath having an elongated casing surrounding at least one channel, said endoscope comprising:

a tip portion having an optics window;

a control handle having a set of controls for controlling the angular orientation of said tip portion;

an insertion tube extending between said tip portion and said control handle, said insertion tube including a resilient, D-shaped tube having a cylindrical portion extending between a substantially planar diameter portion, a braided tube enclosing said D-shaped tube, with the cylindrical portion of said D-shaped tube abutting said braided tube, said braided tube having formed therein a longitudinal groove extending inwardly from said braided tube diametrically opposite said D-shaped tube, and a coating of a flexible, waterproof material tightly surrounding the outer surface of said braided tube; and an imaging system extending through said D-shaped tube from said control handle to said tip portion, whereby said sheath may be installed on said endoscope with said casing surrounding said insertion tube and said tip portion and said channel positioned in said groove.

2. The endoscope of claim 1 wherein said imaging system comprises an eyepiece mounted on said control handle, a first optical fiber extending through the interior of said D-shaped tube from the optics window of said tip portion to said eyepiece, and a second optical fiber extending from the optics window of said tip portion to an external illumination device.

3. The endoscope of claim 1 wherein said imaging system comprises a miniature television camera mounted in said tip portion behind said optics window, an electrical cable extending through said D-shaped tube from said tip portion to said control handle for coupling a video signal generated by said television camera to said control handle, an electrically powered light mounted in said tip portion behind said optics window, and a pair of conductors extending through said D-shaped tube from said tip portion to said control handle for applying electrical power to said light.

4. The endoscope of claim 1, further including a plurality of longitudinally spaced wires extending from one side of said insertion tube to the other adjacent the apexes of said D-shaped tube to prevent said insertion tube from deforming in a direction transverse to the plane of said groove.

5. The endoscope of claim 1, further including a pair of channels formed in said insertion tube within said braided tube on opposite sides of said groove, and a plurality of control cables extending through said channels from said control handle to said tip portion.

6. The endoscope of claim 5, further including a flexible control cable tube surrounding each of said control cables with said channels, and wherein said flexible control cable tubes collectively occupy substantially all of the volume contained within said channels and whereby said control cable tubes substantially prevent the walls of said groove from collapsing.

7. The endoscope of claim 6, further including a filter of resilient material filling any portion of said control channels that is not occupied by said control cable tubes.

8. The endoscope of claim 1, further including a plurality of longitudinally spaced ribs extending between the apexes of said D-shaped tube, said ribs having a pair of semicylindrical walls separated by an inwardly extending, U-shaped section conforming to the shape of said groove, whereby said ribs stabilize said insertion tube and groove responsive to bending of said insertion tube.

9. The endoscope of claim 8 wherein said ribs are welded to said D-shaped tube near the apexes thereof.

10. The endoscope of claim 8 wherein said ribs extend around at least a portion of the outer periphery of the cylindrical portion of said D-shaped tube.

11. The endoscope of claim 1 wherein said D-shaped tube is formed by a plurality of concentric coils of flexible ribbon, with adjacent coils helically wound in opposite directions.

12. The endoscope of claim 1 wherein the portion of said braided tube that forms said groove contacts the diameter portion of said D-shaped tube so that said D-shaped tube can stabilize said groove.

13. An endoscope insertion tube for use with a disposable sheath having an elongated casing surrounding at least one channel, comprising:

a generally cylindrical tube of braided, resilient material having a longitudinally extending groove formed therein configured to receive the channel of said sheath;

a support member extending transversely across said braided tube along a diameter thereof that is generally perpendicular to the plane of said groove, said support member preventing deformation of said tube in said transverse direction;

an imaging system extending through said braided tube on the side of said support member opposite said groove; and a flexible, resilient covering bonded to the outer surface of said braided tube.

14. The insertion tube of claim 13 wherein said support member comprises a resilient tube having a D-shaped cross section, said D-shaped tube being positioned within said braided tube, with a cylindrical portion of said D-shaped tube abutting said braided tube and a generally planar section of said D-shaped tube extending diametrically across said braided tube so that said D-shaped tube divides said braided tube substantially in half.

15. The insertion tube of claim 14 wherein said D-shaped tube is formed by a plurality of concentric coils of flexible ribbon, with adjacent coils helically wound in opposite directions.

16. The insertion of claim 14 wherein the portion of said braided tube that forms said groove contacts the diameter portion of said D-shaped tube so that said D-shaped tube can stabilize said groove.

17. The insertion tube of claim 13, further including a plurality of longitudinally spaced ribs extending between the apexes of said D-shaped tube, said ribs having a pair of semicylindrical walls separated by an inwardly extending, U-shaped section conforming to the shape of said groove, whereby said ribs stabilize said insertion tube and groove responsive to bending of said insertion tube.

18. The insertion tube of claim 17 wherein said ribs are welded to said D-shaped tube near the apexes thereof.

19. The insertion tube of claim 17 wherein said ribs extend around at least a portion of the outer periphery of the cylindrical portion of said D-shaped tube.

20. The insertion tube of claim 13 wherein said support member includes a plurality of longitudinally spaced wires extending from one side of said braided tube to the other to prevent said insertion tube from deforming in a direction transverse to the plane of said groove.

21. The insertion tube of claim 13, further including a pair of channels formed in said insertion tube within said braided tube on opposite sides of said groove, and a plurality of control cables extending through said channels from said control handle to said tip portion.

22. The insertion tube of claim 21, further including a flexible control cable tube surrounding each of said control cables within said channels, and wherein said flexible control cable tubes collectively occupy substantially all of the volume contained within said channels and whereby said control cable tubes substantially prevent the walls of said groove from collapsing.

23. The insertion tube of claim 22, further including a filter of resilient material filling any portion of said control channels that is not occupied by said control cable tubes.

24. A support member for use in the insertion tube of an endoscope, said support member comprising a plurality of concentric coils of resilient ribbon wire arranged with adjacent coils helically wound in opposite directions, each of said coils having a D-shaped cross section.

*25. An endoscope for use with a disposable sheath having an elongated casing and at least one channel extending along said casing, said endoscope comprising:*

*a tip portion having an optics window;*

*a control handle having a set of controls for controlling the angular orientation of said tip portion;*

*an insertion tube extending between said tip portion and said control handle, said insertion tube extending a flexible tube having a non-cylindrical cross-section, a braided tube enclosing said flexible tube, and a coating of a flexible waterproof material tightly surrounding the outer surface of said braided tube; and*

*an imaging system extending through said flexible tube from said control handle to said tip portion, whereby said sheath may be installed on said endoscope with said casing surrounding said insertion tube and said tip portion and said channel positioned against said flexible tube.*

*26. The endoscope of claim 25 wherein said imaging system comprises an eyepiece mounted on said control handle, a first optical fiber extending through the interior of said flexible tube from the optics window of said tip portion to said eyepiece, and a second optical fiber extending from the optics window of said tip portion to an external illumination device.*

*27. The endoscope of claim 25 wherein said imaging system comprises a miniature television camera mounted in said tip portion behind said optics window, an electrical cable extending through said flexible tube from said tip portion to said control handle for coupling a video signal generated by said television camera to said handle, an electrically powered light mounted in said tip portion behind said optics window, and a pair of conductors extending through said flexible tube from said tip portion to said control handle for applying electrical power to said light.*

*28. The endoscope of claim 25 wherein said flexible tube is formed by a plurality of concentric coils of flexible ribbon, with adjacent coils helically wound in opposite directions.*

*29. The endoscope of claim 25 wherein said flexible tube has a generally D-shaped configuration formed by a cylindrical portion extending between opposite longitudinal edges of a substantially planar diameter portion.*

* * * * *

UNITED STATES PATENT AND TRADEMARK OFFICE

CERTIFICATE OF CORRECTION

PATENT NO. : Re. 34,110

DATED : October 27, 1992

INVENTOR(S) : Eric A. Opie et al.

It is certified that error appears in the above-identified patent and that said Letters Patent is hereby corrected as shown below:

In column 10, claim 6, line 39, please delete "with" and substitute therefor --within--.

In column 10, claim 7, line 44, please delete "filter" and substitute therefor --filler--.

In column 11, claim 16, line 32, please insert --tube-- between "insertion" and "of".

In column 12, claim 23, line 9, please delete "filter" and substitute therefor --filler--.

In column 12, claim 25, line 25, please delete "extending" and substitute therefor --including--.

In column 12, claim 27, line 48, please insert --control-- between the second "said" and "handle".

Signed and Sealed this

Nineteenth Day of October, 1993

Bruce Lehman

*Attest:*

BRUCE LEHMAN

*Attesting Officer*

*Commissioner of Patents and Trademarks*